US00PP25137P3

(12) United States Plant Patent
van Rijn

(10) Patent No.: US PP25,137 P3
(45) Date of Patent: Dec. 2, 2014

(54) *BOUGAINVILLEA* PLANT NAMED 'RIJNBO0801'

(50) Latin Name: *Bougainvillea communis*
Varietal Denomination: Rijnbo0801

(71) Applicant: Leonardus van Rijn, de Lier (NL)

(72) Inventor: Leonardus van Rijn, de Lier (NL)

(73) Assignee: RijnPlantBV (NL)

( * ) Notice: Subject to any disclaimer, the term of this patent is extended or adjusted under 35 U.S.C. 154(b) by 105 days.

(21) Appl. No.: 13/573,534

(22) Filed: Sep. 20, 2012

(65) Prior Publication Data

US 2014/0082780 P1 Mar. 20, 2014

(51) Int. Cl.
*A01H 5/00* (2006.01)

(52) U.S. Cl.
USPC ..... Plt./256

(58) Field of Classification Search
USPC ..... Plt./256
See application file for complete search history.

(56) References Cited

PUBLICATIONS

UPOV-PLUTO: Plant Variety Database, 201305, cultivar 'Rijnbo0801'.*

* cited by examiner

*Primary Examiner* — Susan McCormick Ewoldt
(74) *Attorney, Agent, or Firm* — Cassandra Bright

(57) ABSTRACT

A new and distinct *Bougainvillea* cultivar named 'Rijnbo0801' is disclosed, characterized by large, long, white, slightly backwardly arching bracts. Plants produce long, slender foliage. The new variety is a *Bougainvillea*, typically produced as an ornamental plant.

1 Drawing Sheet

Latin name of the genus and species: *Bougainvillea communis.*

Variety denomination: 'Rijnbo0801'.

BACKGROUND OF THE INVENTION

The new cultivar is the product of a planned breeding program. The new variety originated as a seedling selection resulting from the crossing of 2 proprietary *Bougainvillea communis* seedlings identified as '21' as the female or seed parent with '52' as the male or pollen parent.

The new variety was finally selected by the inventor at a commercial greenhouse belonging to the inventor in De Lier, The Netherlands in June of 2008. After this selection the inventor continued confidential testing and propagation of 'Rijnbo0801' for approximately 2 years, assessing stability of the unique characteristics of this variety.

Asexual reproduction of the new cultivar 'Rijnbo0801' was first performed at the commercial greenhouse of the inventor in De Lier, The Netherlands by vegetative cuttings in November of 2008. Access to all plants was restricted, as plants were kept in a greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'Rijnbo0801' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Rijnbo0801'. These characteristics in combination distinguish 'Rijnbo0801' as a new and distinct *Bougainvillea* cultivar:

1. Bracts are large, long and slender.
2. Color of mature bract is bright white.
3. Bracts arch slightly backwards.
4. Leaves are long and slender.

PARENT COMPARISON

Plants of the new cultivar 'Rijnbo0801' are similar to the seed parent, in most horticultural characteristics. The new variety, however, produces bracts that are longer and more slender as well as arching backwards more than seen in the parent variety. The new variety also produces a larger and less dense inflorescence compared to the parent.

Plants of the new cultivar 'Rijnbo0801' are similar to the pollen parent, in most horticultural characteristics. The new variety, however, produces bracts of a different shape and color than the pollen parent.

COMMERCIAL COMPARISON

'Rijnbo0801' is similar in most horticultural characteristics to the known commercial variety *Bougainvillea communis* 'Vera White' U.S. Plant Pat. No. 11,177. However, the new variety produces bracts that are longer than bracts of 'Vera White'. The new variety also produces leaves that are longer and narrower than 'Vera White'.

'Rijnbo0801' is similar in most horticultural characteristics to the variety *Bougainvillea communis* 'Rijnbo710', U.S. Plant Pat. No. 21,009. The new variety produces flowers bracts that are larger and longer than bracts of 'Rijnbo710'.

The new variety produces bracts that are white colored, whereas 'Rijnbo710' produce bracts that are magenta colored. The new variety also produces leaves that are longer and narrower than 'Rijnbo710'.

BRIEF DESCRIPTION OF THE PHOTOGRAPH

The accompanying photograph in FIG. 1 illustrates in full color a typical plant of 'Rijnbo0801' grown in a commercial greenhouse in De Lier, The Netherlands. This plant is approximately 6 months old, shown planted in a 14 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe a 'Rijnbo0801' plant. This plant was grown in a greenhouse in a commercial 17 cm container in De Lier, the Netherlands. The plant described is approximately 1 year old, was not free branching. Branches were regularly pinched and twined on a wooden rack. Temperatures ranged from 15° C. at night and 18° C. to 24° C. during the day. No artificial light, photoperiodic treatments were given to the plants. Measurements and numerical values represent averages of typical plant types.

Botanical classification: *Bougainvillea communis* 'Rijnbo0801'.

PROPAGATION

Time to initiate roots: 14-21 days at approximately 25° C.

Root description: Roots are fine, fibrous and well branched.

PLANT

Growth habit: This plant is an upright tender perennial, suitable for indoor ornamental use, or outdoor garden use in warm climates.

Pot size of plant described: 17 cm.

Height: 60 cm.

Plant spread: 50 cm.

Growth rate: Approximately 20-30 cm/month.

Main stem color: Grey-Brown near RHS 199D with yellow-green stripes near RHS 146A and 146B.

Main stem texture: Smooth.

Branching characteristics: Not free branching, moderate branching can be achieved with pinching.

Length of primary lateral branches: 30-40 cm.

Quantity of primary lateral branches: 2.

Characteristics of primary lateral branches:

- *Diameter*.—Approximately. 0.5 cm.
- *Color*.—Near RHS Yellow-Green 146B with a few Greyed-green stripes near RHS 199D.
- *Texture*.—Dull, smooth.

Internode length: Approximately 2 to 4 cm.

FOLIAGE

Leaf:

- *Arrangement*.—Alternate, simple.
- *Quantity*.—Approximately 12 per branch.
- *Average length*.—Medium approximately. 12.8 cm.
- *Average width*.—Medium approximately 6.4 cm.
- *Shape of blade*.—Elliptical.
- *Apex*.—Acute.
- *Base*.—Obtuse.
- *Margin*.—Entire.
- *Texture of top surface*.—Smooth, glossy.
- *Texture of bottom surface*.—Smooth.
- *Pubescence*.—Upper side foliage: medium density of very short hairs with a length of max. 0.5 mm Color Green-white near RHS157D. Bottom side: Low density of very short hairs.
- *Color*.—Young foliage upper side: Yellow-green near RHS 144A. Young foliage under side: Yellow-green near RHS 144B. Mature foliage upper side: Between RHS Green 137A and RHS green 147A. Mature foliage under side: Near 147B RHS.
- *Venation*.—Type: Pinnate. Venation color upper side: RHS Yellow-Green 144A. Venation color under side: RHS Yellow-Green 144B.
- *Petiole*.—Length: 1.8 cm. Diameter: 0.2 cm. Color: near RHS Yellow-Green 144B. Texture: Smooth.

Other characteristics:

- *Thorns*.—One thorn is above each leaf. Thorn is pointed downwards; Young thorns are soft. Old thorns are very sharp and strong. Average thorn length: 0.8-1.2 cm. Average thorn width at base: 1-3 mm. Thorn coloration: Young thorns near RHS Green 143C. Old thorns RHS Greyed-Orange 166A.

FLOWER

Normal flowering period: Continuously from March to first frost (October).

Inflorescence:

- *Form*.—Axillary, loose to moderately compact cyme.
- *Width of entire inflorescence*.—25 cm.
- *Height of entire inflorescence*.—30-40 cm.
- *Quantity of individual flowers in inflorescence*.—Avg. 27-35.

Rate of flower opening: 12-14 days from bud to fully opened flower.

Flower longevity on plant: 14-21 days.

Quantity of inflorescence per plant: 6-11.

Persistent or self-cleaning: Self-cleaning.

Bud:

- *Shape*.—Oblanceolate with sharp apex.
- *Length*.—0.8 cm.
- *Diameter*.—0.5 cm.
- *Color*.—RHS Yellow-Green 145B (very young stage) to RHS 145C.

Individual true flower:

- *Form/type*.—Single, tubular flowers growing from the base of a single bract. The flowers have no petals or sepals. The individual true "flower" is small, and each cluster of three flowers is surrounded by three bracts. Sometimes the cluster consists of more flowers but the number of bracts is nearly always 3.
- *Diameter*.—0.8-0.9 cm.
- *Depth*.—0.1 cm.
- *Days lasting on plant*.—Approximately one week.

Petals: No petals.

Bracts:

- *Days lasting on plant*.—14, self-cleaning.
- *Shape*.—Acute.

*Length*.—4.5-5 cm.
*Width*.—2.7-3 cm.
*Tip*.—Acute.
*Base*.—Cordate.
*Margin*.—Entire.
*Aspect*.—Undulated.
*Color*.—Under side of immature bract: A color between Yellow-Green 149C and White RHS 155A. Upper side of immature bract: A color between Yellow-Green near RHS 149C and White RHS 155A. Under side of mature bract: White near RHS 155A. Upper side of mature bract: White near RHS 155A. Bract vein color on under side: Yellow-green near RHS 145 A. Bract vein color on upper side: Yellow-green near RHS 145 A.
*Sepals*.—No sepals.

Peduncles:
*Length*.—3.1 cm.
*Diameter*.—0.2 cm.
*Angle*.—Approximately 70-90° to the lateral branch.
*Strength*.—Moderately strong.
*Texture*.—Smooth with very small hairs.
*Color*.—Near RHS Yellow-Green 146A.

Pedicels:
*Arrangement*.—Individual flowers in whorls of 3, together on pedicels. Each individual flower sessile, implanted in a colorful bract.
*Length*.—0.5 cm.
*Diameter*.—0.05-0.1 cm.
*Angle*.—Average angle of 45 degrees.
*Strength*.—Moderately strong.
*Color*.—Yellow Green 146B.

Fragrance: None.

REPRODUCTIVE ORGANS

Stamens:
*Number*.—Average 6, sometimes more or less.

Anthers:
*Length*.—Approximately 0.05 cm.
*Color*.—Near RHS Yellow 12A.
*Pollen*.—Color near RHS 13B. Quantity: Scant.

Pistil:
*Number*.—1.
*Length*.—0.5 cm.
*Style*.—Length: 0.05 cm. Color: RHS 145 C.
*Stigma*.—Shape: Lineate. Color: Near RHS Yellow Green 150C. Ovary Color: Near RHS Yellow Green 144A.

OTHER CHARACTERISTICS

Seeds and fruits: Fruit is a 5 lobed Achene, approximately 0.7 cm long and 0.25 cm wide, colored near Grey-Brown 199B. Seeds not observed.

Disease/pest resistance: Neither resistance nor susceptibility to diseases or pests has been observed in this variety.

Temperature tolerance: Tolerates high temperatures to at least 35 degrees Celsius. When temperature is too low this variety will drop its leaves and bracts. Frost is not tolerated. When roots are frozen completely, the plant will not recover.

Drought tolerance: No drought tolerance. Leaves and bracts will drop off the plant immediately under dry conditions.

What is claimed is:

1. A new and distinct cultivar of *Bougainvillea* plant named 'Rijnbo0801' as herein illustrated and described.

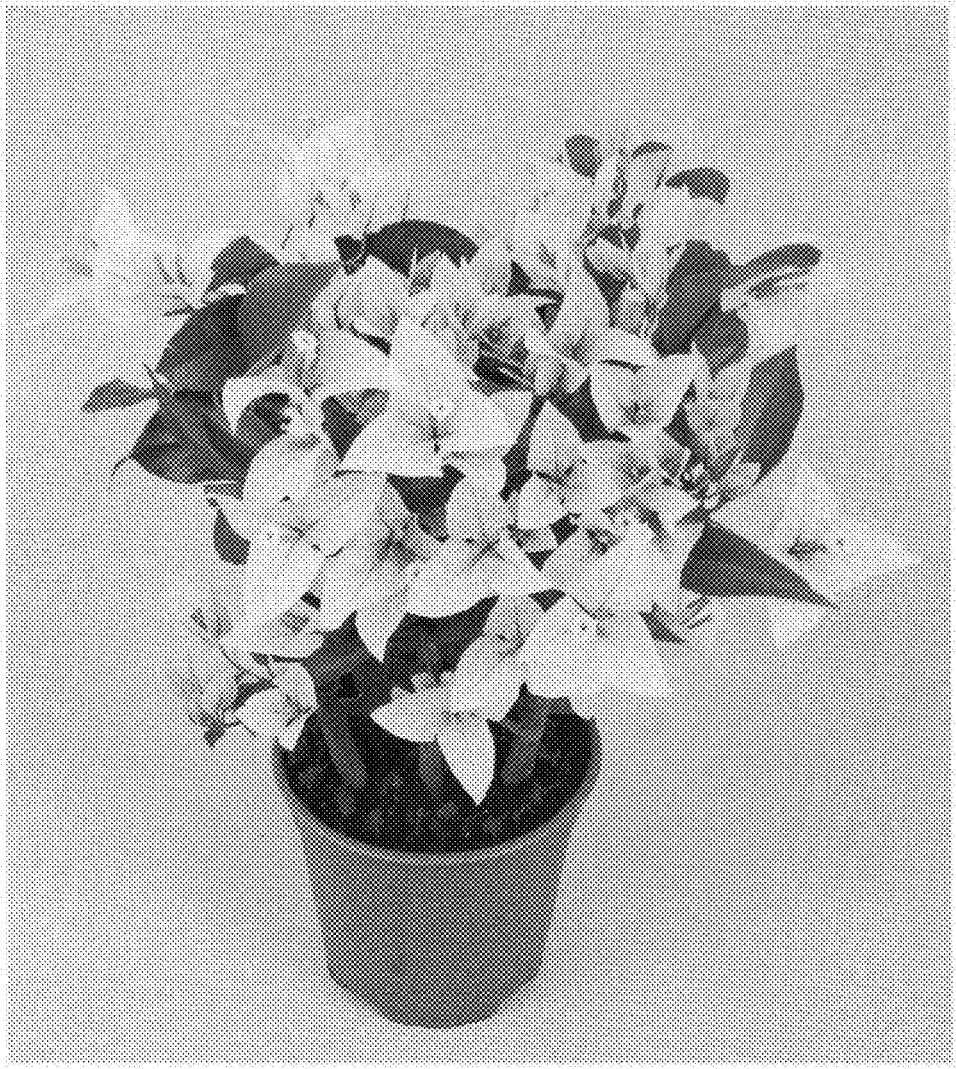

* * * * *